United States Patent [19]

Fischer

[11] 3,965,894
[45] June 29, 1976

[54] MOISTURE TRAP FOR MEDICAL OXYGEN SUPPLY APPARATUS

[76] Inventor: Ernest J. Fischer, 384 Cardiff St., San Bernardino, Calif. 92408

[22] Filed: Jan. 30, 1975

[21] Appl. No.: 545,616

[52] U.S. Cl. .............................. 128/194; 128/203; 128/145.8; 128/142 R; 55/DIG. 17
[51] Int. Cl.² ........................................ A61M 16/00
[58] Field of Search .......... 128/194, 193, 188, 186, 128/187, 191 R, 203, 145.5–145.8, 142–142.3; 55/DIG. 17, 35, 30, 355; 137/204, 181

[56] References Cited
UNITED STATES PATENTS

| | | |
|---|---|---|
| 1,652,309 | 12/1927 | Kingdon ........................ 55/DIG. 17 |
| 2,976,950 | 3/1961 | Smith ............................. 55/DIG. 17 |
| 3,584,621 | 6/1971 | Bird ................................ 128/145.8 |
| 3,667,463 | 6/1972 | Barnes ............................ 128/194 |
| 3,762,409 | 10/1973 | Lester ............................. 128/194 |

Primary Examiner—Robert W. Michell
Assistant Examiner—Henry J. Recla
Attorney, Agent, or Firm—Dana E. Keech

[57] ABSTRACT

Inserted lineally in the output line of an oxygen supply apparatus between the regulator and the humidifier is a moisture trap. This captures moisture borne by a reverse flow of liquid from the humidifier produced by a vacuum occuring in the regulator when the apparatus is shut down and thereby protects minute oxygen flow orifices in the apparatus from impairment by calcification.

4 Claims, 5 Drawing Figures

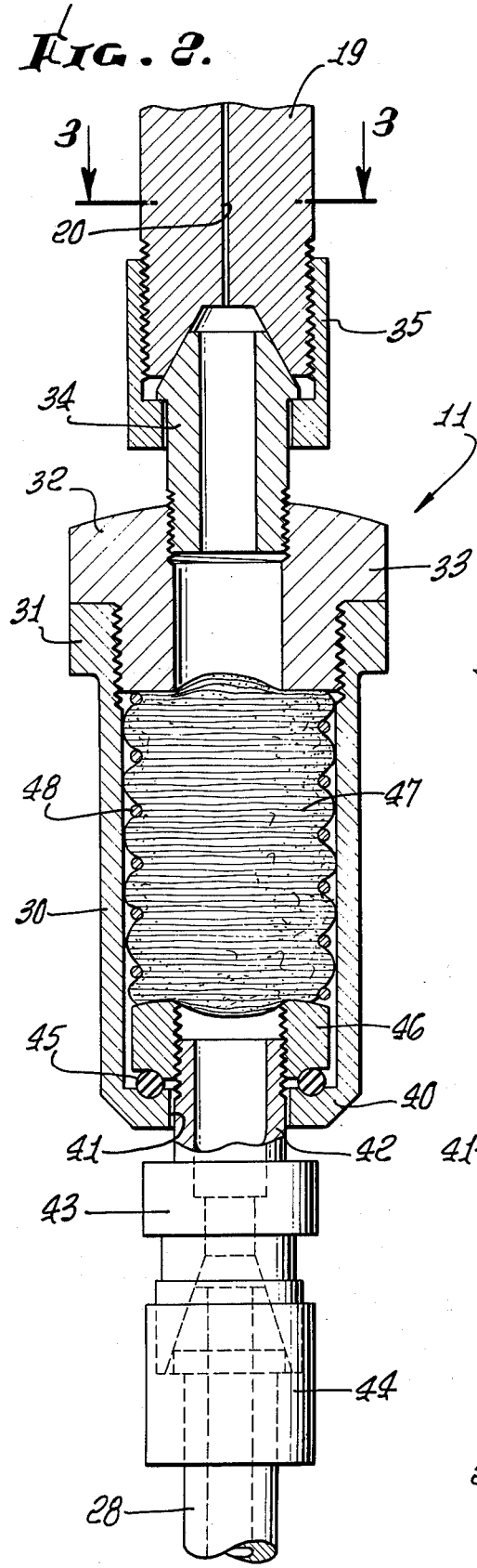
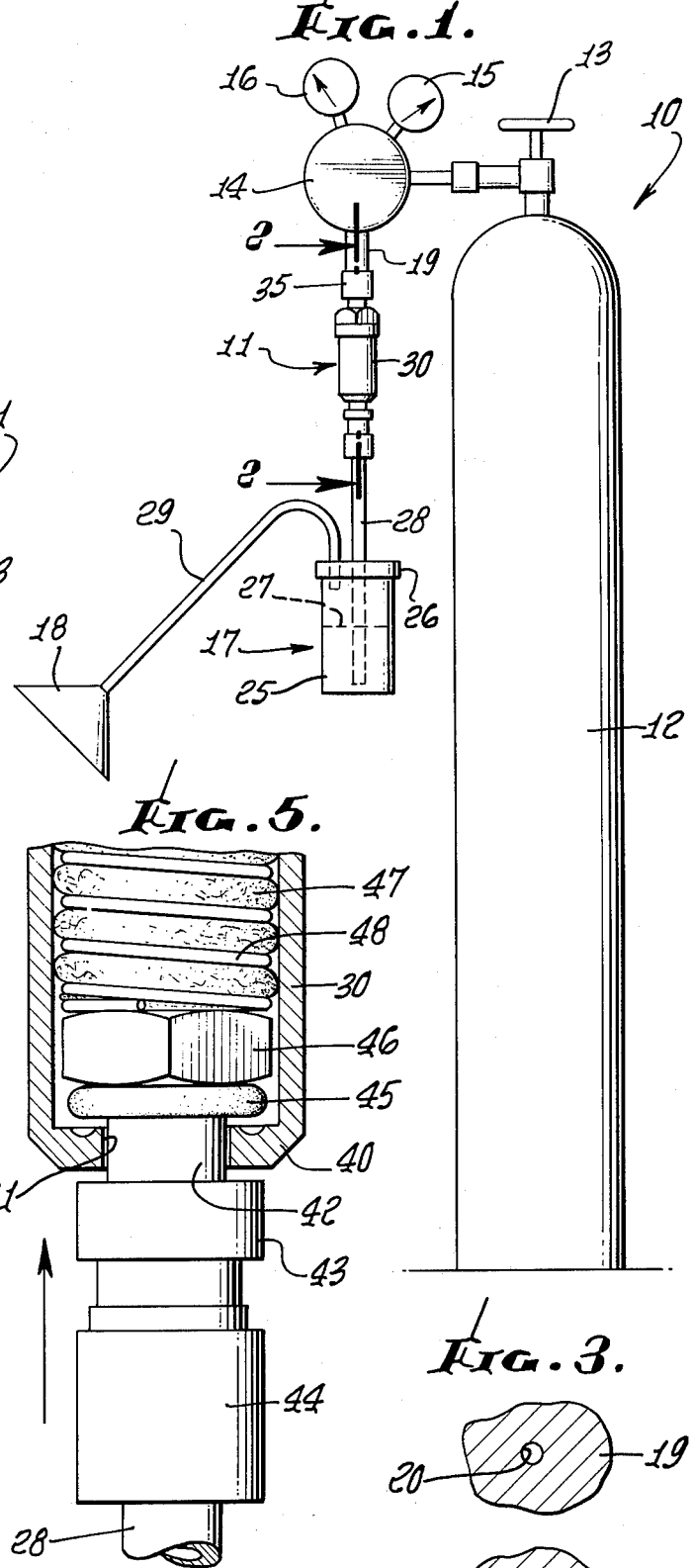
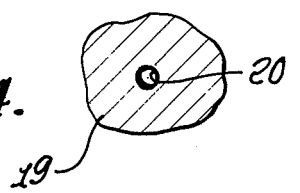

MOISTURE TRAP FOR MEDICAL OXYGEN SUPPLY APPARATUS

SUMMARY OF THE INVENTION

The applicant is engaged in the business of furnishing oxygen supply apparatus to the medical profession and servicing such apparatus to maintain it at a high operating efficiency. A not infrequent cause of impairment of such efficiency in apparatus returned for servicing was discovered to be in the calcification of flow orifices provided in the apparatus for accurately regulating the flow of oxygen therefrom in consonance with specified settings of the control dials thereon. The impairment in this respect was overcome either by drilling out the calcium deposits, if this could be done without increasing the size of the orifices, and, if not, by replacing the parts embodying said orifices.

After being in this business many years, the idea occurred to me that some way might be available for excluding calcium laden moisture from the oxygen measuring orifices of oxygen supply apparatus whereby impairment of their function by calcification could be practically prevented. It is thus an important object of the present invention to provide a water trap for introduction into the oxygen output flow line leading to the humidifier of an oxygen supply apparatus which will effectively inhibit the reverse flow of moisture from said humidifier and thus prevent this reaching the rate of flow measuring orifices of said apparatus.

A further object of the invention is to provide such a water trap which has the capacity to absorb a very substantial quantity of water and confine the same in said trap before any water will be able to bypass said trap and thus gain access to the oxygen rate of flow measuring orifice of the apparatus.

Yet another object of the invention is to provide such a trap having means for readily checking the amount of water captured thereby.

Still another object of the invention is to provide such a trap having means for readily draining from the trap whatever free water captured thereby has collected in the lower end of said trap.

BRIEF DESCRIPTION OF THE DRAWINGS

FIG. 1 is a diagrammatic view of a medical oxygen supply apparatus incorporating a preferred embodiment of the invention.

FIG. 2 is an enlarged vertical sectional view taken on the line 2—2 of FIG. 1 and illustrates the minute size of the rate of flow governing orifice in the regulator of said oxygen supply apparatus, the incidence toward calcification of which orifice, it is the main object of the present invention to overcome.

FIG. 3 is an enlarged fragmentary sectional view taken on the line 3—3 of FIG. 2 and illustrating an oxygen rate of flow measuring orifice in normal operating condition.

FIG. 4 is a view similar to FIG. 3 excepting that the rate of flow governing orifice is shown as calcified and its flow capacity and accuracy thus impaired.

FIG. 5 is a fragmentary operational view of a lower portion of FIG. 2 illustrating the telescopic collapsing of the moisture trap to drain water therefrom.

DETAILED DESCRIPTION OF THE PREFERRED EMBODIMENT

A medical oxygen supply apparatus 10 is diagrammatically disclosed in FIG. 1 in which a preferred embodiment of the moisture trap 11 is incorporated. Besides the moisture trap 11, the apparatus 10 includes an oxygen supply tank 12, having a single outlet controlled by a valve 13, a regulator 14 to which the valve 13 connects, said regulator having in-flow and out-flow pressure guages 15 and 16, an oxygen humidifier 17 and a patient's oxygen receiving mask 18.

The regulator 14 has an externally threaded output stem 19 having a centrally located oxygen rate of flow controlling orifice 20 the diameter of which, as shown in FIG. 2, is minute. The oxygen humidifier 17 includes a canister 25 having a cover 26 holding a body of water 27. Mounted in the cover 26 is a central oxygen inlet pipe 28 which extends to a point close to the bottom of the canister 25 and an oxygen outlet pipe 29, the inner end of which terminates just inside the cover 26 and the outer end of which connects to the oxygen receiving mask 18. The moisture trap 11 connects the oxygen output stem 19 of the regulator 14 to the central oxygen inlet pipe 28 of the humidifier 17 so as to form a relatively free conduit between said elements for the flow of oxygen emitted by the regulator 14, when the valve 13 is turned on, which is discharged at the lower end of pipe 28 and bubbles upwardly through the water 27 so as to be humidified when it is delivered by the outlet pipe 29 to the mask 18. The principal function of the moisture trap 11 (besides its acting as a conduit for oxygen flowing from the regulator to the humidifier) is to prevent a reverse flow of liquid from the humidifier to the regulator when a condition of vacuum occurs in the regulator as a result of valve 13 being shut off. To accomplish these two principal objectives, the moisture trap 11 is preferably constructed as follows:

The main body of the trap comprises a thin walled cylindrical brass shell 30 which is internally threaded at its upper end and provided with an external hexagonal flange 31. Screwed into the upper end of shell 30 is a centrally apertured plug 32 having a hexagonal head 33. A tapered coupling 34 screws into the plug 32 and has an internally threaded bonnet 35 which screws onto regulator output stem 19 to make a tightly sealed connection between the upper end of moisture trap 11 and said stem.

The lower end of shell 30 has an annular internal flange 40 formed thereon as by swedging, said flange having a central opening 41 for receiving a threaded pipe nipple 42 of a pipe fitting 43 which is a part of a union coupling 44 which connects said fitting to the upper end of humidifier central inlet pipe 28.

Inserted in the shell 30 when the moisture trap 11 is being assembled is an O-ring 45, a piston nut 46 which is screwed downwardly on nipple 42 to trap said O-ring between said nut and flange 40 and a moisture absorptive pad 47 having embodied therewith a coil spring 48. The pad 47 and spring 48 are slightly compressed between the plug 32 and piston nut 46 so as to compress O-ring 45 between said nut and the bottom annular flange 40 of shell 30 so that said O-ring seals the lower end of shell 30 and normally prevents the escape of any fluid downwardly past said O-ring. Adjacent surfaces of the nut 46 and flange 40 are turned away in the manufacture of these parts to cause a snug sealing connection to be formed between these and said O-ring when the fitting 43 is permitted to hang freely from the piston nut 46 as shown in FIGS. 1 and 2.

OPERATION

It is to be understood that the view shown in FIG. 1 is strictly diagrammatic and that normally the pipe 28 and the tube 29 are flexible so that there is no rigid connection between the humidifier 17 on the one hand and the moisture trap 11 and the oxygen mask 18 on the other. Thus, there are no forces imposed on the fitting 43 which would disturb the snug fluid tight seal of the lower end of shell 30 effected by the pressure of spring 48 downwardly on piston nut 46 and the O-ring 45.

A flow of oxygen from the apparatus 10 to the mask 18 is effected by opening the valve 13 and the regulator 14 is provided with means for adjusting it to determine the rate at which the oxygen flows from the regulator through the humidifier to the mask. The regulation of the rate of flow of the oxygen effected by the regulator 14 is accomplished by selectively directing said flow through a particular one of a series of minute flow controlling orifices of which the orifice 20 in the output stem 19 of the regulator is an example.

As above pointed out, upon one's shutting off the valve 13 or the regulator in-flow pressure valve 15 at the conclusion of a period of use made of the apparatus 10 in the delivery of oxygen service to the mask 18, there is a tendency for a condition of vacuum to develop within the regulator 14 which tends to suck water from the humidifier 17 into the regulator so that the flow regulating orifice, such as the orifice 20 shown in FIG. 2, is occupied by water which leaves a deposit of calcium on the interior surface of this orifice when the water dries. As illustrated in FIGS. 3 and 4, this calcification greatly reduces the diameter of the flow orifice 20 which is depended upon in the regulator 14 to remain absolutely true to its original manufactured diameter in order for a flow of oxygen at a particular rate to be delivered to the mask 18 at the output pressure indicated by the output guage 16. A calcified flow orifice will substantially decrease the rate of flow actually delivered to the mask 18 as compared with the rate indicated by the guage 16. This fact shows the importance of preventing a reverse flow of water from the humidifier 17 to the regulator 14 in the apparatus 10 and it is the prime object of the present invention to prevent such a reverse flow.

With this end in view, the moisture trap 11 embodies a shell 30 of a substantial volumetric capacity for absorbing and storing water which may be sucked upwardly from the humidifier 17 into the moisture trap 11 and, as a practical matter, will absorb the maximum amount of water which may be expected to be withdrawn upwardly from the humidifier during any given shut-down of the apparatus 10. The absorption pad 47 comprises a short rod of compressed highly absorptive cotton fibrous material which is screwed into the helical spring 48. As water rises through the nipple 42 and nut 46 into contact with the bottom of the pad 47, it is absorbed by said pad and as the level of water in the pad rises by capillary attraction, the excess water flows radially from the pad and downwardly around the piston nut 46.

Operating instructions suggest the lifting on the fitting 43, just before each turning on of the apparatus 10, to withdraw any water collected around the nut 46, as illustrated in FIG. 5. This excess water discharges downwardly into a cloth held around the fitting 43 so that, when use of the apparatus 10 is resumed by opening the valve 13, the flow of oxygen downwardly through the water trap 11 will dry out the water collected in the pad 47 and return this to its originally dry condition. Compliance with the aforesaid instructions, therefore, in the normal use of the apparatus 10, will thus assure that water from the humidifier 17 will be denied access to the regulator 14 and this means that there will no longer be any problem of the oxygen flow control orifice 20 of the regulator 14 becoming calcified.

I claim:

1. In a medical oxygen supply apparatus, the combination of:

an oxygen supply tank;

a valve provided on said tank for dispensing oxygen therefrom;

an oxygen flow regulator connected to said valve and receiving freshly released compressed oxygen therefrom through an in-flow pressure valve and having an output stem means providing a minute flow regulating orifice through which said oxygen is delivered from said flow regulator;

a water trap means having an input conduit connected with said output stem and extending downward therefrom whereby said oxygen delivered therefrom flows downwardly through said water trap means said water trap means lower end having output means;

an oxygen humidifier having an input connected with said output means of said water trap means to receive said flow of oxygen and cause the same to bubble upwardly through a body of water and thus become humidified and having an output means; and oxygen mask means connected to said output means of said humidifier for receiving said humidified oxygen from said humidifier and delivering the same to a patient, said water trap means entrapping water sucked from said humidifier by vacuum occasioned in said regulator by shutting said tank valve or said regulator in-flow valve and thereby protecting said minute oxygen delivery orifice from calcification by said water.

2. A combination as recited in claim 1 wherein said output stem extends downwardly from said regulator to connect with said water trap means and the latter means extends downwardly from said regulator to connect said regulator with said humidifier, and wherein said water trap means embodies a conduit having a passage connecting said humidifier to said regulator; and a highly water absorbent pad, a portion of said passage being enlarged to accommodate therein said pad; and means for having ready access to said passage adjacent to and just below said pad to drain from said passage water that has been absorbed by said pad.

3. A combination as recited in claim 1, wherein said water trap means input conduit includes an enlarged section comprising a cylindrical shell;

a centrally apertured head mounted on and annularly restricting the upper end of said shell, said head providing a connection with said oxygen regulator output stem;

said water trap output means including an inturned flange formed on said shell and annularly restricting the lower end of said shell;

a threaded hollow piston stem extending loosely upwardly through said lower annular flange for limited reciprocation vertically;

a piston nut confined within said shell by said lower flange and screwed on said stem;

an O-ring resting on said lower annular flange and supporting said nut to form a tight seal between said nut and said flange; and a highly absorbent cylindrical pad loosely fitting the space within said shell between said shell head and said piston nut, said hollow piston stem connecting downward with said oxygen humidifier for delivering thereto oxygen flowing downward through said water trap means, said water trap means trapping in said pad water sucked from said humidifier by vacuum occuring in said regulator when said valve is shut, excess captured water being released by lifting said piston nut by pushing up on said hollow piston stem.

4. A combination as recited in claim 3 wherein said pad comprises;

a light stainless coil spring closely fitting within said shell and normally expanding upwardly against said cylinder head and downwardly against said piston nut; and a cylindrical section of closely packed absorbent cotton fiber fitted into said coiled spring so as to fill the latter.

* * * * *